US011028689B2

(12) United States Patent
Zhao et al.

(10) Patent No.: US 11,028,689 B2
(45) Date of Patent: Jun. 8, 2021

(54) METHOD FOR EXPERIMENTALLY DETERMINING THE CONDUCTIVITY OF UNPROPPED FRACTURE IN HYDRAULIC FRACTURING OF SHALE RESERVOIR

(71) Applicant: SOUTHWEST PETROLEUM UNIVERSITY, Chengdu (CN)

(72) Inventors: Zhihong Zhao, Chengdu (CN); Chi Chen, Chengdu (CN); Shouxin Wang, Chengdu (CN); Kun Wang, Chengdu (CN); Cong Lu, Chengdu (CN); Jie Lai, Chengdu (CN); Yuxuan Liu, Chengdu (CN); Ye Zhong, Chengdu (CN); Yuhang Zhao, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 17/005,382

(22) Filed: Aug. 28, 2020

(65) Prior Publication Data

US 2020/0392840 A1 Dec. 17, 2020

(51) Int. Cl.

| | |
|---|---|
| ***E21B 49/00*** | (2006.01) |
| ***G01N 1/28*** | (2006.01) |
| ***G01N 15/08*** | (2006.01) |
| ***G01N 33/24*** | (2006.01) |
| ***G06T 17/30*** | (2006.01) |
| ***G06T 5/00*** | (2006.01) |
| ***G06T 7/62*** | (2017.01) |
| *E21B 43/26* | (2006.01) |

(52) U.S. Cl.
CPC ............ *E21B 49/00* (2013.01); *G01N 1/286* (2013.01); *G01N 15/088* (2013.01); *G01N 33/24* (2013.01); *G06T 5/002* (2013.01); *G06T 7/62* (2017.01); *G06T 17/30* (2013.01); *E21B 43/26* (2013.01); *G01N 2001/2866* (2013.01); *G01N 2015/0846* (2013.01); *G06T 2207/10028* (2013.01); *G06T 2207/30181* (2013.01)

(58) Field of Classification Search
None
See application file for complete search history.

(56) References Cited

U.S. PATENT DOCUMENTS

2015/0355158 A1* 12/2015 Lander ................ G01N 33/385 702/2

* cited by examiner

*Primary Examiner* — Daniel S Larkin

(57) ABSTRACT

The invention discloses a method for experimentally determining the conductivity of an unpropped fracture in hydraulic fracturing of a shale reservoir, comprising: select an outcrop sample with a natural fracture in the shale reservoir, and cut the outcrop sample with along the extension direction of the natural fracture into no less than eight square rock slabs; use a laser scanner to obtain the rough topography data of the fracture surface of each square rock slab and calculate the area tortuosity; pick out the rock samples; model the rough surface of the selected rock samples; import the treated surface model into the engraving machine, and select the downhole core or outcrop rocks in the same horizon for repeated production; calculate the shear slippage at different positions of unpropped fracture according to the data of the shale reservoir; finally test the conductivity of the shale rock samples after shear slip.

5 Claims, 1 Drawing Sheet

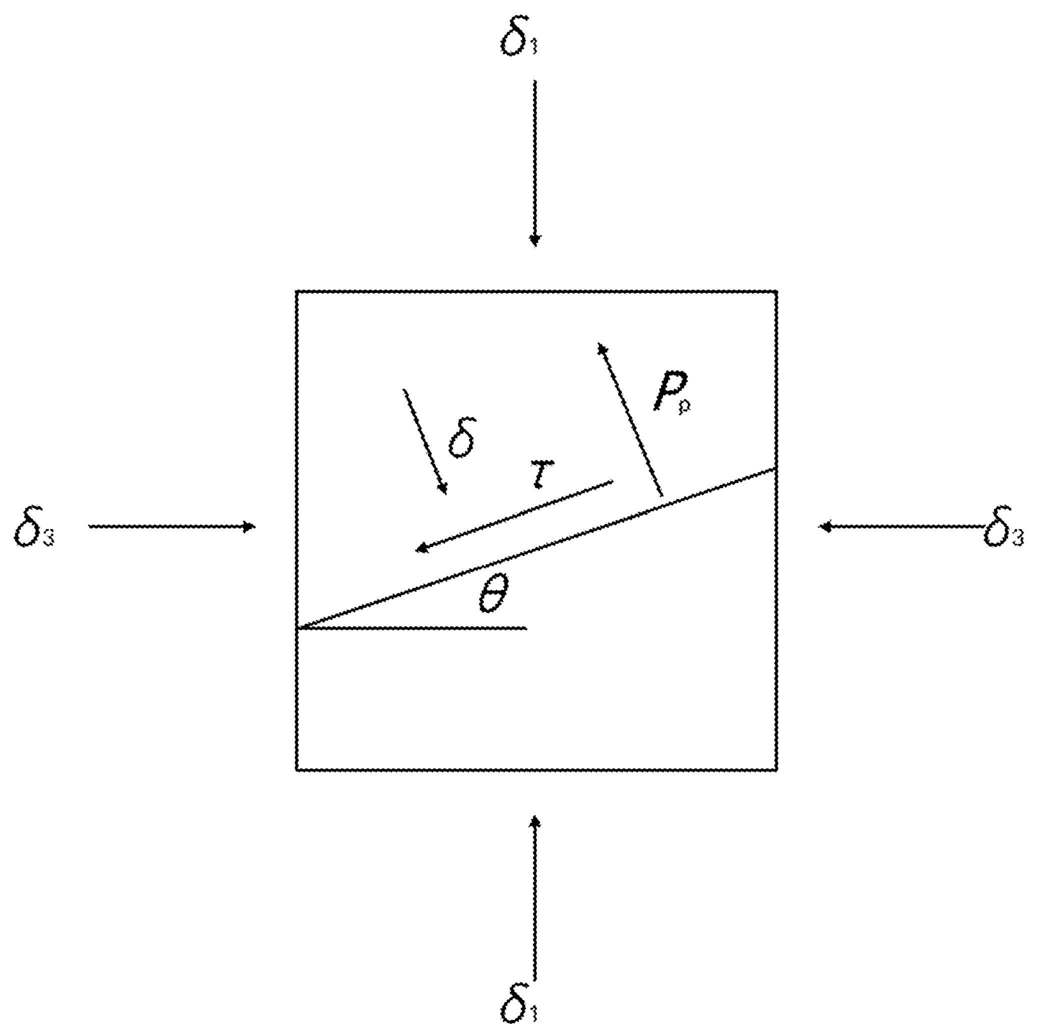
δ1
δ
τ
Pp
δ3
δ3
θ
δ1

METHOD FOR EXPERIMENTALLY DETERMINING THE CONDUCTIVITY OF UNPROPPED FRACTURE IN HYDRAULIC FRACTURING OF SHALE RESERVOIR

BACKGROUND OF THE INVENTION

Field of the Invention

The present invention relates to a method for experimentally determining the conductivity of an unpropped fracture in hydraulic fracturing of a shale reservoir, belonging to the technical field of stimulation and transformation of oil and natural gas reservoirs.

Description of Related Art

Shale gas has become a hot spot in the exploration and development of unconventional resources worldwide, and hydraulic fracturing is an effective method to develop shale gas. It is the core goal of shale fracturing to connect underground natural fracture through hydraulic fracturing and make the natural fracture undergo shear slip under the action of ground stress to form unpropped fractures and thereby construct a fracture network with certain conductivity. The conductivity of unpropped fractures is an important factor affecting productivity. The factors that affect the conductivity of unpropped fracture include rough topography of the fracture surface, shear slippage, mechanical properties of micro-bumps on the fracture surface, and closure stress. How to accurately evaluate the conductivity of unpropped fracture has an important inference on the design of shale gas fracturing scheme and the prediction of post-fracturing productivity.

At present, the conductivity of unpropped fracture is mainly evaluated by experimental testing methods. Specifically, take outcrop sample or downhole core from shale reservoir section, obtain rough fracture surface by manual splitting method, then shear, stagger, combine and package the split rock samples, and apply normal pressure to the fracture surface and test its conductivity to evaluate the conductivity of underground unpropped fractures after hydraulic fracturing.

The problem with this method is that the rough fracture surface obtained by manual splitting is quite different from the rough topography of the natural fracture surface, and its topography cannot represent the natural fracture surface. In addition, different rock samples have different fractures after splitting, there is a great difference in the conductivity test results, and it is not clear which conductivity test results of rough rock samples should be used to represent the conductivity of unpropped fractures in the reservoir. Not only that, the shear slippage of the unpropped fracture has an important influence on the conductivity, and the shear slippage is different at different positions of the unpropped fracture. However, the existing practice is mostly to adopt a fixed shear slippage to represent the slippage of the entire fracture, and use the test data of a point on the fracture to replace the conductivity of the entire fracture. The test conditions are not consistent with the actual conditions of the reservoir.

SUMMARY OF THE INVENTION

In view of the above problems, the present invention mainly overcomes the shortcomings in the prior art, and proposes a method for experimentally determining the conductivity of unpropped fracture in hydraulic fracturing of shale reservoir. In this method, take downhole core or outcrop rocks in the same horizon to produce artificial rock samples with true topography of unpropped fracture surface after hydraulic fracturing in batch by the technology of restructuring the fracture surface, calculate the shear slippage at different positions of the unpropped fracture, shear and stagger the artificial rock samples to obtain shear-slip shale slabs at different positions on the unpropped fracture surface, then test the conductivity test of unpropped fracture, simulate the seepage pattern of unpropped fractures in the shale reservoir after hydraulic fracturing, and accurately evaluate the conductivity and distribution of the unpropped fractures.

The technical solutions provided by the present invention to solve the above technical problems are that a method for experimentally determining the conductivity of unpropped fracture in hydraulic fracturing of shale reservoir comprises the following steps:

Step 1: Collect an outcrop sample with natural fractures in a shale reservoir, and cut the sample into multiple square rock slabs with natural fractures at a length of 142 mm, a width of 37 mm, and a height of 50 mm along the extension direction of the natural fracture; the extension direction of the natural fracture is considered as the length of the slab, and it should be ensured that the height difference between any two points on the natural fracture and the surface of the rock slab is less than 10 mm; the number of square rock slabs is not less than eight;

Step 2: Use a laser scanner to obtain the rough topography data of the square rock slab with natural fractures described in Step 1, and calculate the area tortuosity;

Step 3: Select one square rock slab that best represents the surface topography of the natural fracture in the shale reservoir according to the area tortuosity data obtained in Step 2;

Step 4: Denoise the three-dimensional point cloud data of the square rock slabs selected in Step 3 by standard deviation filtering method, interpolate and normalize the point cloud data by Kriging interpolation method after noise reduction, then import the point cloud data into Geomagic software to convert it into a NURBS surface model, and finally, import the surface model into the engraving machine and use Artcame software that comes with the engraving machine to establish the engraving machine toolpath;

Step 5: Use the downhole core of the shale reservoir section or outcrop rocks in the same horizon to make smooth square slabs with smooth and straight surface, and the rock slab is 142 mm long, 37 mm wide and 30 mm high;

Step 6: Engrave the smooth square rock slabs in Step 5 with an engraving machine into artificial rock samples with uniform surface topography;

Step 7: Calculate the shear slippage of the unpropped fracture by Formula (1), and then divide the fracture into sections by every 0.5 mm of change in slippage from the center of the fracture, and calculate the average slippage of each section;

$$u_s = \left(\frac{k+1}{4G}\right)\left|-\frac{\delta_3-\delta_1}{2}\sin 2\theta\right| l\sqrt{1-(x/l)^2} \tag{1}$$

Where, $u_s$ is the slippage of the unpropped fracture surface, in mm; k is Kolosov constant, k=3-4v; v is Poisson's ratio, dimensionless; G is the shear modulus, in MPa; $\delta_3$ is the maximum horizontal principal stress, in MPa; $\delta_1$ is the minimum horizontal principal stress, in MPa; θ is the angle between the natural fracture and the maximum horizontal principal stress, in °; l is the half-length of the unpropped fracture, in m; and x is the coordinate of any point along the length of the fracture, in m;

Step 8: Shear and stagger the artificial rock samples described in Step 6 in the length direction respectively according to the average shear slippage of each section of the unpropped fracture calculated in Step 7, then use a grinding miller to grind the artificial rock samples at both ends of the length direction to be flush, and bond semi-circular arc-shaped polymethyl methacrylate pads at both ends of the artificial rock sample to obtain shear-slip shale slabs at different positions on the unpropped fracture surface;

Step 9: Determine the closing pressure in the unpropped fracture conductivity test according to the maximum horizontal principal stress, minimum horizontal principal stress, formation pressure, and effective stress coefficient of the shale reservoir, and the calculation formula for the closing pressure in the unpropped fracture conductivity test is Formula (2); determine the experimental temperature of the fracture conductivity test based on the formation temperature;

$$\delta=\frac{\delta_3+\delta_1}{2}-\frac{\delta_3-\delta_1}{2}\cos 2\theta-\alpha P_p \tag{2}$$

Where, δ is the closing pressure, in MPa; $\delta_3$ is the maximum horizontal principal stress, in MPa; $\delta_1$ is the minimum horizontal principal stress, in MPa; θ is the angle between the natural fracture and the maximum horizontal principal stress, in °; α is the effective stress coefficient, in decimal; and $P_p$ is the formation pressure, in MPa.

Step 10: Put the shear-slip shale slabs at different positions on the unpropped fracture surface obtained in Step 8 into the diversion chamber, put the diversion chamber into the conductivity test device, heat the diversion chamber and load the closing pressure according to the closing pressure and experimental temperature determined in Step 9, and test the conductivity of the unpropped fracture at different positions to obtain the conductivity and distribution of unpropped fractures in hydraulic fracturing of shale reservoir.

The further technical solution is that the specific calculation process of area tortuosity in Step 2 is described as follows:

$$R_s=\frac{A_s}{A_n} \tag{3}$$

Where, $R_s$ is the area tortuosity; $A_s$ is the actual area of the rough fracture surface; and $A_n$ is the projected area of the rough fracture surface;

According to the point cloud data of the fracture topography obtained by the laser scanner, the actual area of the rough fracture surface can be calculated in the following way:

$$A_s=\int\left[1+\left(\frac{\partial z(x,y)}{\partial x}\right)^2+\left(\frac{\partial z(x,y)}{\partial y}\right)^2\right]^{1/2}dxdy \tag{4}$$

Where, $A_s$ is the actual area of the rough fracture surface; x is the x-coordinate of the point cloud data; y is the y-coordinate of the point cloud data; and z is the z-coordinate of the point cloud data;

The projected area of the fracture surface is calculated by the following formula:

$$A_n=l\times w \tag{5}$$

Where, $A_n$ is the projected area of the rough fracture surface; l is the length of the rock slab; and w is the width of the rock slab.

The further technical solution is that the square rock slabs in Step 3 are selected by the following steps: calculate the average area tortuosity of multiple square rock slabs, and then select a square rock slab with the area tortuosity closest to the average.

The further technical solution is that the specific calculation process of standard deviation filtering method in Step 4 is described as follows:

(1) Calculate the distance between each point $\{X_n, Y_n, Z_n\}$ and its adjacent eight neighborhood points in the point cloud data array $\{X_i, Y_i, Z_i\}$ of the fracture surface obtained by scanning, and the X and Y coordinates of the neighborhood points are $\{X_{n-1}, Y_{n-1}\}$, $\{X_{n-1}, Y_n\}$, $\{X_{n-1}, Y_{n+1}\}$, $\{X_n, Y_{n-1}\}$, $\{X_n, Y_{n+1}\}$, $\{X_{n+1}, Y_{n-1}\}$, $\{X_{n+1}, Y_n\}$ and $\{X_{n+1}, Y_{n+1}\}$ respectively.

(2) Make statistics of the distance calculated in Step (1), and calculate the average u and standard deviation r of the average distance.

(3) Determine the relationship between the average distance u from the point $\{X_n, Y_n, Z_n\}$ to eight neighborhood points and the distance threshold d=u±5r; if it is greater than the distance d, the noise will be eliminated.

The further technical solution is that the step size is set as 0.1 mm×0.1 mm when the point cloud data is interpolated by Kriging interpolation method in Step 4.

The present invention has the following beneficial effects: select the typical topography of the natural fracture surface of the shale reservoir with a laser scanner, adopt three-dimensional engraving technology to prepare shale sample slabs with uniform surface topography, achieve the accuracy of the samples of no less than 0.02 mm which can meet the requirements of unpropped fracture conductivity test, then divide the shale unpropped fractures into multiple sections in the length direction and calculate the slippage of each fracture section, stagger the rock slabs according to the slippage of each section, and then test the conductivity of unpropped fracture, to obtain the conductivity and distribution of unpropped fractures in hydraulic fracturing of shale reservoir, and work out the conductivity consistent with the reservoir condition.

BRIEF DESCRIPTION OF THE DRAWINGS

FIG. 1 is a stress diagram of unpropped fracture in the embodiments of the present invention.

DESCRIPTION OF THE PREFERRED EMBODIMENTS

The present invention will be further described with the following embodiments and FIGURES.

Embodiment 1

In the present invention, the method for experimentally determining the conductivity of unpropped fracture in hydraulic fracturing of shale reservoir comprises the following steps:

(1) Collect outcrop with natural fractures in a shale reservoir, and use a cutting machine to cut the outcrop into eight square rock slabs with natural fractures at a length of 142 mm, a width of 37 mm, and a height of 50 mm; consider the extension direction of the natural fracture as the length of the slab, make the natural fracture in the middle of the square rock slab, and ensure that the height difference between any two points on the natural fracture and the surface of the rock slab is less than 10 mm;

(2) Separate the eight square rock slabs along the natural fracture, then acquire the rough topography data of the fracture surface of the separated rock slab by a laser scanner, and calculate the area tortuosity of the rough surface of the eight square rock slabs respectively. The result is shown in Table 1.

TABLE 1

Calculation Results of Area Tortuosity

| | No. of Rock Slab | | | | | | | | |
|---|---|---|---|---|---|---|---|---|---|
| | 1 | 2 | 3 | 4 | 5 | 6 | 7 | 8 | Average |
| Area Tortuosity | 1.02 | 1.04 | 1.06 | 1.08 | 1.16 | 1.19 | 1.14 | 1.12 | 1.09 |

(3) According to the calculation data, the area tortuosity of No. 4 rock sample is approximate to the average, so select No. 4 rock sample as the typical rough topography of the unpropped fracture in the shale reservoir interval of Well N201.

(4) Denoise, interpolate and normalize the 3D point cloud data of No. 4 rock sample, and then import the point cloud data into Geomagic software to convert it into a NURBS surface model, and finally, import the surface model into the engraving machine and use Artcame software that comes with the engraving machine to establish the engraving machine toolpath;

(5) Cut the shale outcrop without natural fracture collected in step (1) into square rock samples at a length of 142 mm, a width of 37 mm, and a height of 30 mm by a cutting machine, and engrave the topography of No. 4 rock sample on the cut square rock samples by an engraving machine to obtain artificial rock samples with uniform topography.

(6) According to the geological data of Well N201, the maximum horizontal principal stress is 57.45 MPa, the minimum horizontal principal stress is 47.7 MPa, and the reservoir shear modulus G=24,201.6 MPa. According to imaging logging, the half length of the natural fracture is 1=9 m, and the angle between the natural fracture and the maximum horizontal principal stress is 30°.

Calculate the shear slippage of the unpropped fracture by Formula (1), and then divide the fracture into sections by every 0.5 mm of change in slippage from the center of the fracture, and calculate the average slippage of each section;

TABLE 2

Shear Slippage at Different Positions of the Fracture

| Distance (a, m) between the center point of each section and the fracture center | Shear slippage ($u_s$, m) | Qty. of Sections | Average slippage (u, mm) per section |
|---|---|---|---|
| 0 | 0.00584 | First section | 5.7 |
| 0.5 | 0.005831 | | |
| 1 | 0.005804 | | |
| 1.5 | 0.005758 | | |
| 2 | 0.005694 | | |
| 2.5 | 0.00561 | | |
| 3 | 0.005506 | | |
| 3.5 | 0.00535 | | |
| 3.5 | 0.00535 | Second section | 5 |
| 4 | 0.00523 | | |
| 4.5 | 0.00505 | | |
| 5 | 0.00485 | | |
| 5 | 0.00485 | Third section | 4.6 |
| 5.5 | 0.00462 | | |
| 6 | 0.00435 | | |
| 6 | 0.00435 | Fourth section | 4 |
| 6.5 | 0.004039 | | |
| 7 | 0.00377 | | |
| 7 | 0.00377 | Fifth section | 3.5 |
| 7.5 | 0.00323 | | |
| 7.5 | 0.00323 | Sixth section | 3 |
| 8 | 0.00268 | | |
| 8 | 0.00268 | Seventh section | 2.3 |
| 8.5 | 0.001919 | | |
| 8.5 | 0.001919 | Eighth section | 1 |
| 9 | 0 | | |

(7) Stagger the artificial rock samples engraved in Step (5) by shear slip according to the shear slippage calculated in Step (6), then use a grinding miller to grind the artificial rock samples at both ends of the length direction to be flush, and bond semi-circular arc-shaped polymethyl methacrylate pads at both ends of the artificial rock sample to obtain shear-slip shale slabs at different positions on the unpropped fracture surface;

(8) According to the geological data of Well N201, it is known that the formation temperature of the shale reservoir is 89° C., so it is determined that the conductivity test temperature of the unpropped fracture is 89° C. According to the rock stress measurement, it is determined that the minimum horizontal principal stress is 47.7 MPa and the maximum horizontal principal stress is 57.45 MPa. It is learned from the outcrop profile that the angle between the natural fracture and the maximum horizontal principal stress is 30°, the formation pressure is 55 MPa, and the effective stress coefficient is 0.5. The closing pressure of the conductivity test of unpropped fracture is determined as 22.63 MPa.

(9) Set the temperature of the diversion chamber according to the test temperature set in step (8), set the loading pressure of the pressure testing machine according to the closing pressure set in Step (8), and test the conductivity at different positions (sections) of unpropped fracture.

TABLE 3

Testing Data of Flow Conductivity

| S/N | Temperature (° C.) | Closing Pressure (MPa) | Qty. of Sections | Shear slippage (mm) | Flow conductivity ($\mu m^2 \cdot cm$) |
|---|---|---|---|---|---|
| 1 | 89 | 22.63 | 1 | 5.7 | 94.23 |
| 2 | 89 | 22.63 | 2 | 5 | 71.47 |
| 3 | 89 | 22.63 | 3 | 4.6 | 62.67 |
| 4 | 89 | 22.63 | 4 | 4 | 54.83 |
| 5 | 89 | 22.63 | 5 | 3.5 | 33.66 |
| 6 | 89 | 22.63 | 6 | 3 | 23.17 |
| 7 | 89 | 22.63 | 7 | 2.3 | 15.33 |
| 8 | 89 | 22.63 | 8 | 1 | 10.92 |

The above are not intended to limit the present invention in any form. Although the present invention has been disclosed as above with embodiments, it is not intended to limit the present invention. Those skilled in the art, within the scope of the technical solution of the present invention, can use the disclosed technical content to make a few changes or modify the equivalent embodiment with equivalent changes. Within the scope of the technical solution of the present invention, any simple modification, equivalent change and modification made to the above embodiments according to the technical essence of the present invention are still regarded as a part of the technical solution of the present invention.

What is claimed is:

1. A method for experimentally determining a conductivity of an unpropped fracture in hydraulic fracturing of a shale reservoir, comprising the following steps:

Step 1: Collect an outcrop sample with a natural fracture in the shale reservoir, and cut the sample into no less than eight square rock slabs with the natural fracture along an extension direction of the natural fracture; the extension direction of the natural fracture is considered as the length of the slab, which ensures that a height difference between any two points on the natural fracture and a fracture surface of each square rock slab is less than 10 mm;

Step 2: Use a laser scanner to obtain a rough topography data of the fracture surface of each square rock slab, and calculate an area tortuosity;

Step 3: Select one square rock slab that represents a surface topography of the natural fracture in the shale reservoir according to the area tortuosity obtained in Step 2;

Step 4: Denoise a point cloud data of each square rock slab selected in Step 3 by standard deviation filtering method, interpolate and normalize the point cloud data by a Kriging interpolation method after noise reduction, then import the point cloud data into Geomagic software to convert the point cloud data into a Non-uniform rational basis spline (NURBS) surface model, and finally, import the surface model into an engraving machine and use a computer-aided manufacturing (CAM) software that comes with the engraving machine to establish an engraving machine toolpath;

Step 5: Use a downhole core of the shale reservoir or an outcrop rock in a formation on an identical horizontal plane to make smooth square slabs with smooth and straight surfaces;

Step 6: Engrave the smooth square rock slabs in Step 5 with the engraving machine to produce artificial rock samples with uniform surface topography;

Step 7: Calculate a shear slippage of the unpropped fracture by the following formula, and then divide the fracture into sections by every 0.5 mm of change in slippage from the center of the fracture, and calculate an average shear slippage of each section;

$$u_s = \left(\frac{k+1}{4G}\right)\left|-\frac{\delta_3-\delta_1}{2}\sin 2\theta\right| l\sqrt{1-(x/l)^2}$$

Where, $u_s$ is the shear slippage of the unpropped fracture surface, in mm; k is Kolosov constant, k=3-4v; v is Poisson's ratio, dimensionless; G is a shear modulus, in MPa; $\delta_3$ is a maximum horizontal principal stress, in MPa; $\delta_1$ is a minimum horizontal principal stress, in MPa; θ is the angle between the natural fracture and the maximum horizontal principal stress, in °; l is a half-length of the unpropped fracture, in m; and x is a coordinate of any point along the length of the fracture, in m;

Step 8: Shear and stagger the artificial rock samples described in Step 6 in the length direction respectively according to the average shear slippage of each section of the unpropped fracture calculated in Step 7, then use a grinding miller to grind the artificial rock samples at both ends of the length direction to be flush, and bond semi-circular arc-shaped polymethyl methacrylate pads at both ends of the artificial rock sample to obtain shear-slip shale slabs at different positions on the unpropped fracture surface;

Step 9: Determine a closing pressure in an unpropped fracture conductivity test according to the maximum horizontal principal stress, minimum horizontal principal stress, formation pressure, and effective stress coefficient of the shale reservoir, and determine an experimental temperature of the fracture conductivity test based on a formation temperature; and Step 10: Put the shear-slip shale slabs at different positions on the unpropped fracture surface obtained in Step 8 into a diversion chamber, put the diversion chamber into a conductivity test device, heat the diversion chamber and load the closing pressure according to the closing pressure and experimental temperature determined in Step 9, and test the conductivity of the unpropped fracture at different positions to obtain the conductivity and a distribution of unpropped fractures in hydraulic fracturing of the shale reservoir.

2. The method for experimentally determining the conductivity of an unpropped fracture in hydraulic fracturing of a shale reservoir according to claim 1, wherein a specific calculation process of the area tortuosity in Step 2 is described as follows:

$$R_s = \frac{A_s}{A_n}$$

Where, $R_s$ is the area tortuosity; $A_s$ is an actual area of the rough fracture surface; and $A_n$ is a projected area of the rough fracture surface;

According to the point cloud data of the surface topography obtained by the laser scanner, the actual area of the rough fracture surface can be calculated in the following way:

$$A_s = \int\left[1+\left(\frac{\partial z(x,y)}{\partial x}\right)^2+\left(\frac{\partial z(x,y)}{\partial y}\right)^2\right]^{1/2} dxdy$$

Where, $A_s$ is the actual area of the rough fracture surface; x is the x-coordinate of the point cloud data; y is the y-coordinate of the point cloud data; and z is the z-coordinate of the point cloud data;

The projected area of the fracture surface is calculated by the following formula:

$$A_n = l \times w$$

Where, $A_n$ is the projected area of the rough fracture surface; l is the length of the rock slab; and w is the width of the rock slab.

3. The method for experimentally determining the conductivity of an unpropped fracture in hydraulic fracturing of a shale reservoir according to claim 1, wherein the square rock slab in Step 3 is selected by the following steps: calculate an average area tortuosity of the square rock slabs, and then select the square rock slab with the area tortuosity closest to the average area tortuosity.

4. The method for experimentally determining the conductivity of an unpropped fracture in hydraulic fracturing of a shale reservoir according to claim 1, wherein the specific calculation process of standard deviation filtering method in Step 4 is described as follows:

(1) Calculate the distance between each point $\{X_n, Y_n, Z_n\}$ and its adjacent eight neighborhood points in the point cloud data $\{X_i, Y_i, Z_i\}$ of the fracture surface obtained by scanning, and the X and Y coordinates of the neighborhood points are $\{X_{n-1}, Y_{n-1}\}$, $\{X_{n-1}, Y_n\}$, $\{X_{n-1}, Y_{n+1}\}$, $\{X_n, Y_{n-1}\}$, $\{X_n, Y_{n+1}\}$, $\{X_{n+1}, Y_{n-1}\}$, $\{X_{n+1}, Y_n\}$ and $\{X_{n+1}, Y_{n+1}\}$ respectively;

(2) Make statistics of the distance calculated in Step (1), and calculate the average u and standard deviation r of an average distance; and (3) Determine a relationship between the average distance u from the point $\{X_n, Y_n, Z_n\}$ to eight neighborhood points and a distance threshold $d=u\pm5r$; if the average distance u is greater than the distance threshold d, a noise will be eliminated.

5. The method for experimentally determining the conductivity of an unpropped fracture in hydraulic fracturing of a shale reservoir according to claim 4, wherein a step size is set as 0.1 mm×0.1 mm when the point cloud data is interpolated by the Kriging interpolation method in Step 4.

* * * * *